United States Patent [19]

Hindley

[11] Patent Number: 5,391,565
[45] Date of Patent: Feb. 21, 1995

[54] OXAZOLIDINE DIONE DERIVATIVES

[75] Inventor: Richard M. Hindley, Epsom, England

[73] Assignee: Beecham Group p.l.c., Brentford, England

[21] Appl. No.: 978,706

[22] PCT Filed: Aug. 5, 1991

[86] PCT No.: PCT/GB91/01337

§ 371 Date: Feb. 3, 1993

§ 102(e) Date: Feb. 3, 1993

[87] PCT Pub. No.: WO92/02520

PCT Pub. Date: Feb. 20, 1992

[30] Foreign Application Priority Data

Aug. 6, 1990 [GB] United Kingdom ............. 9017218

[51] Int. Cl.$^6$ ............................... C07D 413/12
[52] U.S. Cl. .................................. 514/375; 514/256;
514/275; 514/340; 514/367; 514/370; 514/376;
544/326; 544/330; 546/275; 546/280; 548/161;
548/193; 548/222; 548/226
[58] Field of Search ............. 548/222, 226; 514/375, 514/376

[56] References Cited

U.S. PATENT DOCUMENTS

| 4,367,234 | 1/1983 | Schnur | 548/226 |
| 5,002,953 | 3/1991 | Hindley | 514/275 |
| 5,037,842 | 8/1991 | Goldstein | 514/375 |

FOREIGN PATENT DOCUMENTS

| 0097453 | 1/1984 | European Pat. Off. . |
| 0306228 | 3/1989 | European Pat. Off. . |
| 2083810 | 3/1982 | United Kingdom . |

OTHER PUBLICATIONS

Chem.+Pharma. Bulletin vol. 30 No. 10. Oct. 1982. Tokyo, JP: T. Sohda et al. pp. 3563-3573.

Primary Examiner—Donald G. Daus
Attorney, Agent, or Firm—Charles M. Kinzig; Stephen Venetianer; Edward T. Lentz

[57] ABSTRACT

Compounds of the formula:

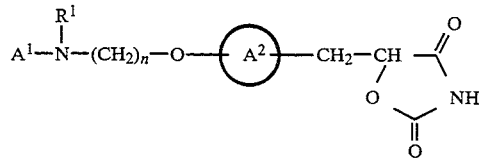

or tautomeric forms and a pharmaceutically acceptable salt, and pharmaceutically acceptable solvates thereof, wherein:

$A^1$ is a substituted or unsubstituted oxazole substituted by up to 4 substituents selected from the group consisting of $C_{1-6}$-alkyl, $C_{1-6}$-alkoxy, phenyl, and halogen or any two substituents on adjacent carbon atoms, together with the carbon atoms to which they are attached, form a benzene ring, and wherein the carbon atoms of the benzene ring represented by the said two substituents are unsubstituted or substituted with up to three groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}$-alkyl, $C_{1-6}$-alkylcarbonyloxy, and $C_{1-5}$-alkylcarbonyl;

$R^1$ is a hydrogen atom, a $C_{1-6}$-alkyl group, a $C_{1-6}$-alkylcarbonyloxy group, a phenyl-$C_{1-6}$-alkyl group, wherein the phenyl moiety may be substituted or unsubstituted, or a substituted or unsubstituted phenyl group, wherein the said phenyl groups may be substituted with up to three groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}$-alkyl, $C_{1-6}$-alkylcarbonyloxy, and $C_{1-6}$-alkylcarbonyl;

$A^2$ is a benzene ring having in total up to five substituents wherein three optional substituents are selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl. $C_{1-6}$-alkoxycarbonyl-$C_{1-6}$-alkyl, $C_{1-6}$-alkylcarbonyloxy, and $C_{1-6}$-alkylcarbonyl; and n is an integer from 2 to 6, are disclosed as hypoglycemics, hypolipidemics and antihypertensives.

9 Claims, No Drawings

OXAZOLIDINE DIONE DERIVATIVES

OXAZOLIDINE DIONE DERIVATIVES

This invention relates to certain substituted oxazolidinedione derivatives, to a process for preparing such compounds, to pharmaceutical compositions containing such compounds and to the use of such compounds and compositions in medicine.

European Patent Applications, Publication Numbers 0008203, 0139421, 0155845, 0177353, 0193256, 0207581, 0208420 and 0306228 relate to thiazolidinedione derivatives which are disclosed as having hypoglycaemic and hypolipidaemic activity. Chem. Pharm. Bull 30 (10) 3580–3600 also relates to certain thiazolidinedione derivatives having hypoglycaemic and hypolipidaemic activities.

It has now surprisingly been discovered that certain novel substituted-oxazolidinedione derivatives show improved blood-glucose lowering activity and they are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

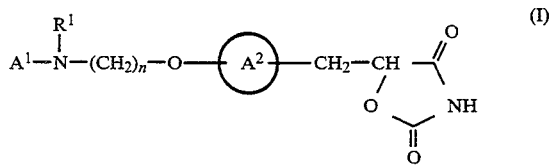

or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substituents; and n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur or nitrogen.

Favoured aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2, or 3 heteroatoms, especially 1 or 2, selected from oxygen, sulphur or nitrogen.

Suitable values for $A^1$ when it represents a 5- membered aromatic heterocyclyl group include thiazolyl and oxazolyl, especially oxazolyl.

Suitable values for $A^1$ when it represents a 6- membered aromatic heterocyclyl group include pyridyl or pyrimidinyl.

Preferably, $A^1$ represents a moiety of formula (a), (b) or (c):

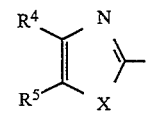

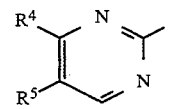

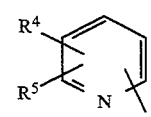

wherein: $R^4$ and $R^5$ each independently represents a hydrogen atom, an alkyl group or a substituted or unsubstituted aryl group or when $R^4$ and $R^5$ are each attached to adjacent carbon atoms, then $R^4$ and $R^5$ together with the carbon atoms to which they are attached form a benzene ring wherein each carbon atom represented by $R^4$ and $R^5$ together may be substituted or unsubstituted; and in the moiety of formula (a) X represents oxygen or sulphur.

Aptly, $A^1$ represents a moiety of the abovedefined formula (a).

Aptly, $A^1$ represents a moiety of the abovedefined formula (b).

Aptly, $A^1$ represents a moiety of the abovedefined formula (c).

In one favoured aspect $R^4$ and $R^5$ together represent a moiety of formula (d):

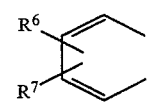

wherein $R^6$ and $R^7$ each independently represent hydrogen, halogen, substituted or unsubstituted alkyl or alkoxy.

Suitably, $R^6$ and $R^7$ each independently represent hydrogen, halogen, alkyl or alkoxy.

Favourably, $R^6$ represents hydrogen. Favourably, $R^7$ represents hydrogen.

Preferably, $R^6$ and $R^7$ both represent hydrogen.

In a further favoured aspect $R^4$ and $R^5$ each independently represent hydrogen, alkyl or a substituted or unsubstituted phenyl group and more favourably, $R^4$ and $R^5$ each independently represent hydrogen, alkyl or phenyl.

Preferably, for the moiety of formula (a), $R^4$ and $R^5$ together represent the moiety of formula (d).

Preferably, for the moieties of formula (b) or (c), $R^4$ and $R^5$ both represent hydrogen.

Suitable substituents for the moiety $A^2$ include halogen, substituted or unsubstituted alkyl or alkoxy.

Favourably, $A^2$ represents a moiety of formula (e):

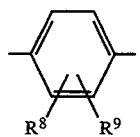

wherein $R^8$ and $R^9$ each independently represent hydrogen, halogen, substituted or unsubstituted alkyl or alkoxy.

Suitably, $R^8$ and $R^9$ each independently represent hydrogen, halogen, alkyl or alkoxy.

Preferably, $R^8$ and $R^9$ each represent hydrogen.

Favourably, X represents oxygen. Favourably, X represents sulphur.

In one preferred aspect the present invention provides a class of compounds, which fall wholly within the scope of formula (I), of formula (II):

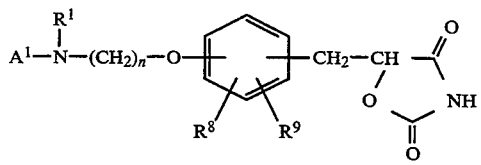

or a tautomeric form thereof, and/or a pharmaceutically acceptable salt thereof and/or a pharmaceutically acceptable solvate thereof, wherein $A^1$, $R^1$ and n are as defined in relation to formula (I) and $R^8$ and $R^9$ are as defined in relation to formula (e).

Suitably, n represents an integer 2, 3, or 4, notably 2 or 3 and especially 2.

Suitably, $R^1$ represents hydrogen alkyl, acyl, especially acetyl, or benzyl.

Preferably, $R^1$ represents a methyl group.

As indicated above a compound of formula (I) may exist in one of several tautomeric forms, all of which are encompassed by the present invention. It will be appreciated that the present invention encompasses all of the isomeric forms of the compounds of formula (I) and the pharmaceutically acceptable salts thereof, including any stereoisomeric forms thereof, whether as individual isomers or as mixtures of isomers.

Suitable substituents for any heterocyclyl group include up to 4 substituents selected from the group consisting of: alkyl, alkoxy, aryl and halogen or any two substituents on adjacent carbon atoms, together with the carbon atoms to which they are attached, may form an aryl group, preferably a benzene ring, and wherein the carbon atoms of the aryl group represented by the said two substituents may themselves be substituted or unsubstituted.

When used herein the term 'aryl' includes phenyl and naphthyl optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

When used herein the terms 'alkyl' and 'alkoxy' relate groups having straight or branched carbon chains, containing up to 12 carbon atoms.

Suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups.

Suitable substituents for any alkyl group include those indicated above in relation to the term "aryl".

When used herein the term 'acyl' refers to organic acyl groups such as alkylcarbonyloxy groups for example $C_{1-6}$ alkylcarbonyloxy groups.

Suitable pharmaceutically acceptable salts include salts of the oxazolidinedione moiety, and, where appropriate, salts of carboxy groups.

Suitable pharmaceutically acceptable salts of the oxazolidinedione moiety include metal salts especially alkali metal salts such as the lithium, sodium and potassium salts.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable solvates include hydrates.

In a further aspect the present invention also provides a process for the preparation of a compound of formula (I), or a tautomeric form thereof, and/or a pharmaceutically acceptable salt thereof, and/or a pharmaceutically acceptable hydrate thereof, which process comprises reacting a compound of formula (III):

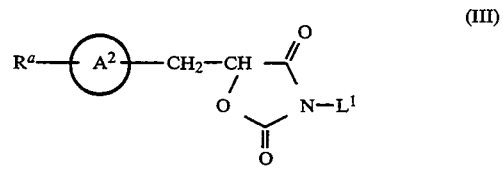

wherein $A^2$ is as defined in relation to formula (I), $L^1$ is a hydrogen atom or a protecting group, and $R^a$ is a moiety convertible to a moiety of formula (f):

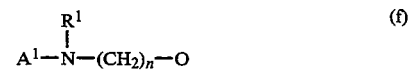

wherein $R^1$, $A^1$ and n are as defined in relation to formula (I) with an appropriate reagent capable of converting $R^a$ to the said moiety (f) and thereafter, if required, carrying out one or more of the following optional steps:

(i) converting a compound of formula (I) to a further compound of formula (I);

(ii) preparing a pharmaceutically acceptable salt of the compound of formula (I) and/or a pharmaceutically acceptable solvate thereof.

Suitably, $R^a$ represents $R^1HN-(CH_2)_n-O-$ wherein $R^1$ and n are as defined in relation no formula (I) or $R^a$ represents a hydroxyl group.

When $R^a$ is $R^1HN—(CH_2)_n—O—$, an appropriate reagent capable of converting $R^a$ to a moiety (f) is a compound of formula (IV):

$$A^1—R^x \qquad (IV)$$

wherein $A^1$ is as defined in relation to formula (I) and $R^x$ represents a leaving group.

A suitable leaving group $R^x$ includes a halogen atom, preferably a chlorine or bromine atom, or a thioalkyl group for example a thiomethyl group.

Preferably, $L^1$ represents a protecting group, suitably a benzyl group.

The reaction between the compound of formula (III) and the appropriate reagent may be carried out under conditions suitable to the particular compound of formula (III) and the reagent chosen. Thus for example the abovementioned reaction between a compound of formula (III) wherein $R^a$ represents $R^1HN—(CH_2)_n—O—$ and the compound of formula (IV), may be carried out in any suitable solvent, for example tetrahydrofuran, at a temperature in the range of between 0° and 60° C.

Conversions of $R^a$ to the moiety of formula (f) may be effected via single step or multiple step conversions, using appropriate conventional chemistry.

Examples of multiple step conversions include the conversion of $R^a$ when representing a hydroxyl group into a moiety $R^1HN—(CH_2)_n—O—$ and thereafter conversion to the moiety (f).

Thus, when $R^a$ represents OH the conversion of $R^a$ into $R^1HN(CH_2)_n—O—$ may conveniently be carried out by coupling a compound of the abovedefined formula (III) with a compound of formula (V):

$$R^1NR^y(CH_2)_n—OH \qquad (V)$$

wherein $R^1$ and n are as defined in relation to formula (I) and $R^y$ is hydrogen or a nitrogen protecting group, in the presence of a suitable coupling agent; and thereafter, if required, removing any nitrogen protecting group.

A suitable coupling agent for the coupling reaction between the compound of formula (III) and (V) is provided by diethylazodicarboxylate and triphenylphosphine. The coupling reaction may be carried out in any suitable solvent at a low to medium temperature, for example in tetrahydrofuran at a temperature in the range of between 0° and 60° C.

Conversion of $R^1HN—(CH_2)_n—O—$ into a moiety of formula (f) may be effected as described above.

Alternatively, when $R^a$ is hydroxyl, conversion into a moiety of formula (f) is suitably effected by treating the compound of the abovedefined formula (III) with a compound of formula (VI):

$$A^1—\underset{\underset{R^1}{|}}{N}—(CH_2)_n—OR^z \qquad (VI)$$

wherein $A^1$, $R^1$ and n are as defined in relation to formula (I) and $R^z$ represents hydrogen or a tosylate or mesylate group.

The reaction between the compound of formula (III) wherein $R^a$ is a hydroxyl group and the reagent of the abovedefined formula (VI), when $R^z$ is hydrogen, may suitably be carried out in an aprotic solvent, such as tetrahydrofuran, at low to medium temperature, for example at ambient temperature, and preferably in the presence of a coupling agent such as that provided by triphenylphosphine and diethylazodicarboxylate.

The reaction between the compound of formula (III), wherein $R^a$ is a hydroxyl group, and the reagent of the abovedefined formula (VI) when $R^z$ is tosylate or mesylate may be carried out in an aprotic solvent, such as dimethylformamide, at a low to elevated temperature, for example in the range of from 50° C. to 120° C. and preferably in the presence of a base, such as sodium hydride.

The compound of formula (VI) when $R^z$ is tosylate or mesylate may be prepared from the corresponding compound of formula (VI) when $R^z$ is hydrogen by reaction with either a tosyl halide or a mesyl halide in a solvent such as pyridine.

The reagent of formula (VI) may be prepared by reacting a compound of the hereinabove defined formula (IV), with a compound of the hereinbefore defined formula (V) and thereafter if required removing any nitrogen protecting group using the appropriate conventional conditions.

The reaction between the compounds of formula (IV) and (V) may be carried out under any suitable conditions, such as in solvent, for example in an aprotic solvent such as tetrahydrofuran, at a low to medium temperature, for example a temperature in the range of from 0° to 60° C.

Favourably when $R^1$ represents hydrogen the reaction is carried out using the compound of formula (V) as a solvent at a low to elevated temperature, suitably an elevated temperature such as in the range of between 100° and 170° C.

A compound of formula (III) wherein $R^a$ is OH may be prepared by reacting a compound of formula (VII):

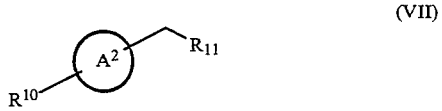

(VII)

wherein $A_2$ is as defined in relation to formula (I), $R^{10}$ represents a hydroxyl group or a protected hydroxyl group and $R^{11}$ represents a group or moiety convertible into an oxazolidinedione group, with a reagent capable of converting a moiety $R^{11}$ into an oxazolidinedione group; and thereafter if required removing any protecting group.

Suitably, $R^{10}$ represents a protected hydroxy group, for example a benzyloxy group.

Suitably $R^{11}$ represents a moiety of formula (g):

$$—\underset{\underset{OH}{|}}{CH}—CO_2R^{12} \qquad (g)$$

wherein $R^{12}$ represents a $C_{1-6}$ alkyl group, suitably a methyl group.

When $R^{11}$ represents a moiety of formula (g), a suitable reagent is urea.

Reaction conditions for the reaction between the compound of formula (VII) and the reagent will of course depend upon the particular nature of $R^{11}$ and the reagent, for example when $R^{11}$ is a moiety of formula (g) and the reagent is urea, the reaction may be carried out in an alkanoic solvent, such as ethanol, at any temperature providing an acceptable rate of formation of the required product, for example an elevated temperature, preferably the reflux temperature of the solvent; preferably the reaction is effected in the presence of a base, such as a alkali metal alkoxide, for example sodium methoxide, followed by treatment with a dilute mineral acid, for example dilute hydrochloric acid.

The compounds of formula (VII) are known compounds or they may be prepared according to methods used to prepare known compounds, for example the compounds of formula (VII) wherein $R^{11}$ is a moiety (g) may be prepared according to methods disclosed in Chem. Pharm. Bull. 30. (1982), 3563.

The abovementioned conversion of a compound of formula (I) into a further compound of formula (I) includes the conversion of one group $R^1$ into another group $R^1$.

The conversion of a compound of formula (I) to a further compound of formula (I) may be carried out by using any appropriate conventional procedure.

Suitable conversions of one group $R^1$ into another group $R^1$ includes converting hydrogen into an acyl group.

The conversion of a compound of formula (I) wherein $R^1$ represents hydrogen into a compound of formula (I) wherein $R^1$ represents acyl may be carried out using any appropriate conventional acylation procedure, such as by treating an appropriately protected compound of formula (I) with an acylating agent. For example acetic anhydride may be used to prepare the compound of formula (I) wherein $R^1$ is acetyl.

The compounds of formula (IV) and (V) are known commercially available compounds or are prepared using methods analogous to those used to prepare known compounds.

Suitable protecting groups in any of the abovementioned reactions are those used conventionally in the art. Thus, for example, a suitable nitrogen protecting group is a benzyl group or a benzyloxycarbonyl group and a suitable hydroxyl protecting group is a benzyl group.

The methods of formation and removal of such protecting groups are those conventional methods appropriate to the molecule being protected. Thus for example a benzyloxy group may be prepared by treatment of the appropriate compound having a hydroxyl group with a benzyl halide, such as benzyl bromide, and thereafter when required the benzyl group may be conveniently removed using a mild ether cleavage reagent such as trimethylsilyliodide.

Where appropriate the isomeric forms of the compounds of formula (I) and the pharmaceutically acceptable salts thereof may be prepared as individual isomers using conventional chemical procedures.

As mentioned above the compounds of the invention are indicated as having useful therapeutic properties:

The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt thereof and/or a pharmaceutically acceptable solvate thereof for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

The following Procedures and Examples illustrate the invention but do not limit it in any way.

EXAMPLE 1

5-(4-[2-((N-methyl-N-(2-benzoxazolyl)amino)ethoxy]-benzyl)-2,4-oxazolidinedione

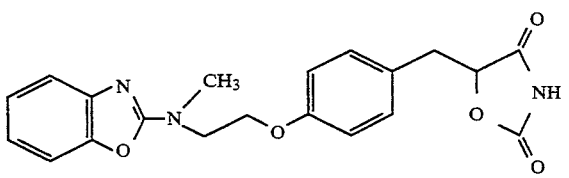

Sodium hydride (0.85 g; 60% dispersion in oil) was added portionwise to a stirred solution of 5-[(4-hydroxy)benzyl]oxazolidine-2,4-dione (2 g) in dry DMF (65 ml) under an atmosphere of nitrogen. After effervescence had ceased, 2-(N-(2-benzoxazolyl)-N-methylamino)ethanol methanesulphonyl ester (2.73 g) was added and the solution heated to 80° C. overnight. After cooling the mixture was added to water (400 ml), neutralised (2M HCl) and extracted with ethyl acetate (3×200 ml). The combined organic extracts were washed with water (100 ml), brine (2×100 ml), dried (MgSO4) and evaporated to dryness. Chromatography of the residue on silica gel in 1% methanol in dichloromethane afforded the title compound (m.p. 173°-4° C.; MeOH).

$^1$H NMR δ (DMSO-d$_6$) 2.9-3.15 (2H, complex); 3.2 (3H, s); 3.85 (2H, t); 4.25 (2H, t); 5.2 (1H, complex); 6.8-7.4 (8H, complex); 11.7 (1H, broad s, exchanges with D$_2$O).

PREPARATION 1

Methyl 2-chloro-3-(4-benzyloxy)phenylpropionate

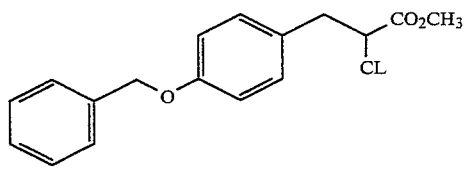

To a cooled (below 5° C.) and stirred suspension of (4-benzyloxy) aniline hydrochloride (12 g) in acetone (120 ml), 1,4-dioxan (20 ml) and concentrated hydrochloric acid (11 ml) was added dropwise a solution of sodium nitrite (4 g) in water (10 ml) over a period of 10 minutes. The suspension was stirred below 5° C. for a further 30 minutes, then methyl acrylate (28 ml) was added dropwise over 2 minutes, and the suspension allowed to warm to 30° C. Copper (I) iodide (0.3 g) was now added portionwise to the mixture, which was left to stir for a further hour. Excess solvent was evaporated off, the residue partitioned between water (500 ml and ethyl acetate, the organic extracts (3×200 ml) combined and washed with dilute ammonia solution (2×200 ml), water (200 ml) , brine (200 ml), dried (MgSO4), filtered and evaporated to dryness. The title compound was obtained as an oil.

$^1$H NMR δ (CDCl$_3$) 3.0-3.45 (2H, complex); 3.8 (3H, s); 4.45 (1H, t); 5.1 (2H, s); 6.95 (2H, d); 7.25 (2H, d); 7.5 (5H, complex).

PREPARATION 2

2-Hydroxy-3-(4-benzyloxy)phenylpropionic acid

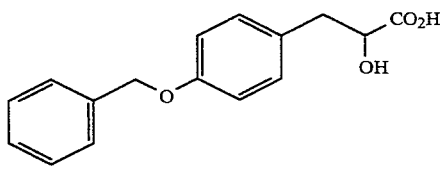

Methyl-2-chloro-3-(4-benzyloxy)phenylpropionate (9g),sodium hydroxide (1.27 g) and calcium carbonate (2.95 g) were refluxed in a mixture of 1,4-dioxan (50 ml) and water (80 ml) for 16 hours. After cooling the mixture was acidified (2M HCl; 200 ml) and extracted with ethyl acetate (2×200 ml). The combined organic extracts were washed with brine (2×100 ml) , dried (MgSO4) , filtered and evaporated. The title compound (mp 145°-5° C.) was obtained following recrystallization of the organic residues from ethyl acetate/hexane.

$^1$H NMR δ (CDCl$_3$+DMSO-d$_6$) 2.6-3.1 (2H, complex); 4.2 (1H, complex); 5.0 (2H, s); 6.8-6.9 (2H, d); 7.1-7.5 (7H, complex); 6.7-8.0 (2H, v broad s; exchanges with D$_2$O).

PREPARATION 3

Ethyl 2-hydroxy-3-(4-benzyloxy)phenylpropionate

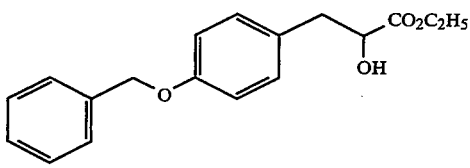

2-hydroxy-3-(4-benzyloxy)phenylpropionic acid (4 g) and concentrated hydrochloric acid (0.1 ml) were refluxed in ethanol (70 ml) for 16 hours. The solution was cooled, added to water (400 ml) and extracted with ethyl acetate (2×200 ml). The combined organic extracts were washed with brine (2×100 ml), dried (MgSO$_4$), filtered and evaporated to dryness to afford the title compound, which was used in the next stage without further purification.

$^1$H NMR δ (CDCl$_3$) 1.3 (3H, t), 2.8 (1H, broad s, exchanges with D$_2$O), 2.8-3.2 (2H, complex); 4.2 (2H, q); 4.35 (1H, multipier); 5.1 (2H, s); 6.9 (2H, d); 7.2 (2H, d); 7.45 (5H, s).

PREPARATION 4

5-[(4-Benzyloxy)benzyl]oxazolidine-2,4-dione.

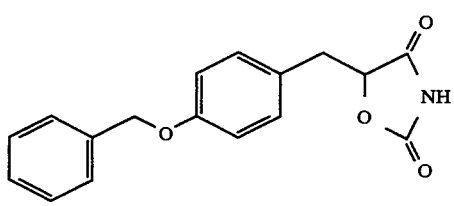

A solution of ethyl 2-hydroxy-3-(4-benzyloxy)phenyl-propionate (4.5 g), urea (1.62 g) and sodium methoxide (1.13 g) in a mixture of methanol (4 ml) and ethanol (40 ml) was stirred for 2 hours at room temperature, then refluxed for 3 hours. After cooling, the mixture was added to hydrochloric acid (2M; 260 ml) and extracted with ethyl acetate (2×250 ml). The combined organic extracts were washed with water (200 ml), brine (200 ml), dried (MgSO$_4$), filtered and evaporated to dryness. The residue was chromatographed on silica gel in 5% methanol in dichloromethane to afford the title compound (m.p.140° C.).

$^1$H NMR δ (CDCl$_3$+DMSO-d$_6$) 2.9-3.3 (2H, complex); 5.0 (1H, t); 5.05 (2H, s); 6.85-7.0 (2H, d); 7.1-7.25 (2H, d); 7.45 (5H, s) 7.2-7.7 (1H, broad s, exchanges with D$_2$O).

PREPARATION 5

5-[(4-Hydroxy)benzyl]oxazolidine-2,4-dione.

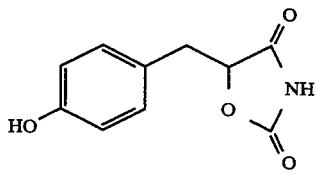

A solution of 5-[4-benzyloxy)benzyl]-oxazolidine-2,4-dione (4.7 g) in dry 1,4-dioxan (70 ml) in the presence of 10% palladium on charcoal (0.25 g) was stirred under an atmosphere of hydrogen at ambient temperature until hydrogen uptake ceased. The solution was filtered through diatomaceous earth, the filter pad was washed exhaustively with dioxan, and the combined filtrates evaporated to dryness under vacuum. The residue was chromatographed on silica-gel in 10% methanol in dichloromethane to afford the title compound (m.p. 205° C.).

NMR δ (DMSO-d$_6$) 2.8-3.2 (2H, complex); 5.2 (1H, t); 6.65-6.75 (2H, d); 7.0-7.1 (2H, d); 9.5 (2H, broad s, exchanges with D$_2$O).

DEMONSTRATION OF EFFICACY OF COMPOUNDS

Obese Mice, Oral Glucose Tolerance Test.

C57 bl/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 7 mice were used for each treatment.

| EXAMPLE NO: | LEVEL IN DIET (μmol kg$^{-1}$ of DIET) | % REDUCTION IN AREA UNDER BLOOD GLUCOSE CURVE |
|---|---|---|
| 1 | 300 | 41 |

Toxicology

No toxicological effects were indicated for any of the compounds of the invention in any of the abovementioned tests.

I claim:

1. A compound of formula (I):

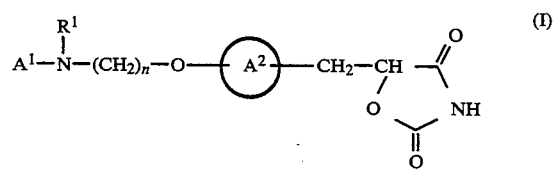

or a tautomeric form thereof and/or a pharmaceutically acceptable salt thereof, and/or a pharmaceutically acceptable solvate thereof, wherein:

A$^1$ represents a substituted or unsubstituted oxazole substituted by up to 4 substituents selected from the group consisting of C$_{1-6}$-alkyl, C$_{1-6}$-alkoxy, phenyl and halogen or any two substituents on adjacent carbon atoms, together with the carbon atoms to which they are attached, form a benzene ring, and wherein the carbon atoms of the benzene ring represented by the said two substituents are unsubstituted or substituted with up to three groups selected from halogen, C$_{1-6}$-alkyl, phenyl, C$_{1-6}$-alkoxy, halo-C$_{1-6}$-alkyl, hydroxy, amino, nitro, carboxy, C$_{1-6}$-alkoxycarbonyl, C$_{1-6}$-alkoxycarbonyl-$C_{1-6}$-alkyl, $C_{1-6}$-alkylcarbonyloxy and $C_{1-6}$-alkylcarbonyl;

$R^1$ represents a hydrogen atom, a $C_{1-6}$-alkyl group, a $C_{1-6}$-alkylcarbonyloxy group, a phenyl-$C_{1-6}$-alkyl group, wherein the phenyl moiety may be substituted or unsubstituted, or a substituted or unsubstituted phenyl group, wherein the said phenyl groups may be substituted with up to three groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}$-alkyl, $C_{1-6}$-alkylcarbonyloxy and $C_{1-6}$-alkylcarbonyl;

$A^2$ represents a benzene ring having in total up to five substituents wherein three optional substitutents are selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}$-alkyl, $C_{1-6}$-alkylcarbonyloxy and $C_{1-6}$-alkylcarbonyl; and n represents an integer from 2 to 6.

2. A compound according to claim 1, wherein $A^1$ represents a moiety of formula (a):

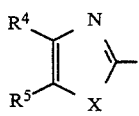

wherein X represents oxygen;

$R^4$ and $R^5$ each independently represents a hydrogen atom, a $C_{1-6}$-alkyl group, a phenyl group or a phenyl group substituted with up to three groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}$-alkyl, $C_{1-6}$-alkylcarbonyloxy and $C_{1-6}$-alkylcarbonyl; or when $R^4$ and $R^5$ are each attached to adjacent carbon atoms, then $R^4$ and $R^5$ together with the carbon atoms to which they are attached form a benzene ring wherein each carbon atom represented by $R^4$ and $R^5$ together may be unsubstituted or unsubstituted with up to three groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}$-alkyl, $C_{1-6}$-alkylcarbonyloxy and $C_{1-6}$-alkylcarbonyl.

3. A compound according to claim 1, wherein $R^4$ and $R^5$ together represent a moiety of formula (d):

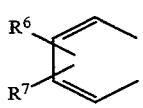

wherein $R^6$ and $R^7$ each independently represent hydrogen, halogen, $C_{1-6}$-alkyl, $C_{1-6}$-alkoxy, or $C_{1-6}$-alkyl or $C_{1-6}$-alkoxy substituted with up to three, groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-5}$-alkyl, $C_{1-6}$-alkylcarbonyloxy and $C_{1-6}$-alkylcarbonyl.

4. A compound according to claim 1, wherein $A^2$ represents a moiety of formula (e):

wherein $R^8$ and $R^9$ each independently represent hydrogen, halogen, $C_{1-6}$-alkyl, $C_{1-6}$-alkoxy, or $C_{1-6}$-alkyl or $C_{1-6}$alkoxy substitutedwith up to three, groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}C_{1-6}$-alkylcarbonyloxy, and $C_{1-6}$-alkylcarbonyl.

5. A compound according to claim 1, of formula (II):

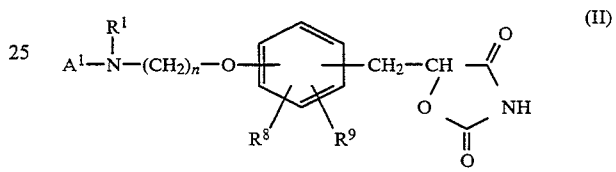

or a tautomeric form thereof, and/or a pharmaceutically acceptable salt thereof and/or a phamaceutically acceptable solvate thereof, wherein $A^1$, $R^1$ and n are as defined in relation to formula (I) and $R^8$ and $R^9$ each independently represent hydrogen, halogen, $C_{1-6}$-alkoxy, $C_{1-6}$-alkyl or $C_{1-6}$-alkyl substituted with up to three groups selected from halogen, $C_{1-6}$-alkyl, phenyl, $C_{1-6}$-alkoxy, halo-$C_{1-6}$-alkyl, hydroxy, amino, nitro, carboxy, $C_{1-6}$-alkoxycarbonyl, $C_{1-6}$-alkoxycarbonyl-$C_{1-6}$-alkyl, $C_{1-6}$-alkylcarbonyloxy, and $C_{1-6}$-alkylcarbonyl.

6. A compound according to claim 1, wherein n represents an integer 2, 3 or 4.

7. A compound according to claim 1, being 5-(4-[2-((N-methyl-N-(2-benzoxazolyl)amino)ethoxy]benzyl)-2,4-oxazolidinedione; or a tautomeric form thereof or a pharmaceutically acceptable salt thereof, or a pharmaceutically acceptable solvate thereof.

8. A pharmaceutical composition comprising a compound according to claim 1, or a tautomeric form thereof, or a pharmaceutically acceptable salt thereof, or a pharmaceutically acceptable solvate thereof, and a pharmaceutically acceptable carrier therefor.

9. A method for the treatment and/or prophylaxis of hyperglycaemia or hyperlipidaemia in a human or non-human mammal which comprises administering an effective, non-toxic amount of a compound of formula (I), or a tautomeric form thereof and/or a pharmaceutically acceptable salt thereof and/or a pharmaceutically acceptable solvate thereof to a hyperglycaemic human or non-human mammal in need thereof.

* * * * *